United States Patent [19]

Camaggi et al.

[11] Patent Number: 5,221,792
[45] Date of Patent: Jun. 22, 1993

[54] DERIVATIVES FROM 3,4-DEHYDRO-PIPERIDIN-5-ONE EXHIBITING A HERBICIDAL ACTIVITY

[75] Inventors: Giovanni Camaggi, Novara; Giovanni Meazza, Saronno; Ciro Preziuso, Opera, all of Italy

[73] Assignee: Agrimont S.p.A., Milan, Italy

[21] Appl. No.: 830,902

[22] Filed: Feb. 4, 1992

Related U.S. Application Data

[62] Division of Ser. No. 482,720, Feb. 21, 1990, Pat. No. 5,149,359.

Foreign Application Priority Data

Feb. 21, 1989 [IT] Italy .................. 19498 A/89

[51] Int. Cl.[5] .................. C07D 211/74; C07D 211/86
[52] U.S. Cl. .................. 546/296; 546/288; 546/293; 546/219; 546/242
[58] Field of Search .................. 546/296, 293, 288

[56] References Cited

U.S. PATENT DOCUMENTS 4,387,230  6/1983  White et al. .................. 546/302
4,636,510  1/1987  Schneider et al. .................. 546/296

FOREIGN PATENT DOCUMENTS 081938  6/1979  Japan .................. 546/297

*Primary Examiner*—Alan L. Rotman
*Attorney, Agent, or Firm*—Stevens, Davis, Miller & Mosher

[57] ABSTRACT

There are described compounds exhibiting a herbicidal action of general formula:

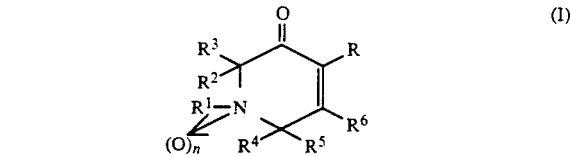

in which:
R

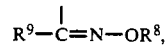

(where, $R^9$=alkyl, phenyl, substituted phenyl, naphthyl, cycloalkyl; $R^8$=alkyl, haloalkyl, alkenyl, haloalkenyl, alkynyl, substituted phenyl, aralkyl, cycloalkyl;
$R^2$, $R^3$, $R^4$, $R^5$=H, alkyl, haloalkyl;
$R^6$=—$OR^{11}$, (where: $R^{11}$=H, alkaline or alkaline earth metal;
$R^1$=phenyl, substituted phenyl, aralkyl, cycloalkyl, the —$OR^{18}$ group (where $R^{18}$=alkyl, phenyl, substituted phenyl, aralkyl, substituted aralkyl), the

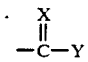

group (where X=O, S and Y=phenyl, substituted phenyl, heterocycle, alkyl, haloalkyl, cycloalkyl, —$R^{19}$—$X^1$—$R^{20}$, —X—$R^{21}$, —$R^{22}$—$X^1$—$R^{23}$—$X^2$—$R^{24}$, —$NR^{25}R^{26}$, wherein: $R^{19}$=alkyl $C_1$-$C_{16}$, aralkyl; $R^{20}$=alkyl $C_1$-$C_{16}$, haloalkyl, alkenyl, alkynyl, cycloalkyl, phenylalkyl $C_7$-$C_{13}$, phenyl; $R^{21}$=alkyl $C_1$-$C_{16}$, haloalkyl, alkenyl $C_3$-$C_8$, alkynyl, cycloalkyl, aralkyl, aryl, substituted aryl, —$R^{19}$—$X^1$—$R^{20}$; $R^{22}$,$R^{23}$, $R^{24}$, like or unlike are $C_1$-$C_{16}$ alkyls;
$R^{25}$,$R^{26}$, like or unlike are: H, alkyl $C_1$-$C_6$, alkoxyl $C_1$-$C_6$, phenyl, substituted phenyl; $X^1$, $X^2$ like or unlike are O, S, SO, $SO_2$); n=0, 1, on condition that when n=1, $R^1$=phenyl, substituted phenyl, aralkyl; cycloalkyl.

1 Claim, No Drawings

DERIVATIVES FROM 3,4-DEHYDRO-PIPERIDIN-5-ONE EXHIBITING A HERBICIDAL ACTIVITY

This is a division of application Ser. No. 482,720, filed Feb. 21, 1990, now U.S. Pat. No. 5,149,359.

DESCRIPTION OF THE INVENTION

The present invention relates to derivatives of 3,4-dehydro-piperidin-5-one having herbicidal activity.

Therefore, an object of the present invention concerns compounds having general formula (I):

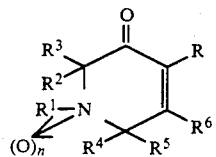

wherein:
R = —CO—R$^7$,

—NH—COR$^{10}$ (where R$^7$, R$^9$ = alkyl C$_1$-C$_6$, cycloalkyl, naphthyl, phenyl, substituted phenyl with halogens —CN, —NO$_2$, —CH$_3$, —SOCH$_3$, —OCH$_3$, CF$_3$; R$^8$ = alkyl C$_1$-C$_6$, alkyl C$_1$-C$_6$ containing 1-4 halogens, alkenyl C$_2$-C$_6$, alkenyl C$_2$-C$_6$ containing 1-4 halogens, alkynyl C$_3$-C$_6$, cycloalkyl C$_3$-C$_7$, heterocycle with 5 or 6 atoms, aralkyl C$_7$-C$_{20}$, phenyl, phenyl substituted with halogens, —CN, —NO$_2$, —CH$_3$, —O—CH$_3$, —CF$_3$; R$^{10}$ = phenyl, phenyl substituted with halogens —CN, —NO$_2$, —CH$_3$, —OCH$_3$, —CF$_3$);

R$^2$, R$^3$, R$^4$, R$^5$ = like or unlike one another, are H, alkyl C$_1$-C$_3$, alkyl C$_1$-C$_3$ substituted with 1-4 halogens; R$^6$ = OR$^{11}$,

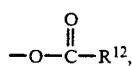

—S(O)$_m$—R$^{13}$, —NR$^{14}$R$^{15}$, halogen,

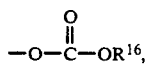

—O—S(O)$_q$—R$^{17}$ (where: R$^{11}$ = H, alkaline or alkaline-earth metal; R$^{12}$, R$^{13}$ are alkyl C$_1$-C$_6$ optionally substituted with 1-11 halogens, cycloalkyl C$_3$-C$_6$, aralkyl C$_7$-C$_{20}$, phenyl, phenyl substituted with halogens, —CN, —NO$_2$, —CH$_3$, —OCH$_3$, —CF$_3$, dialkyl amino; m, q are 0, 1, 2; R$^{14}$, R$^{15}$, like or unlike are H, alkyl C$_1$-C$_6$, alkoxyl C$_1$-C$_6$; R$^{16}$ = alkyl C$_1$-C$_6$, alkenyl C$_2$-C$_6$, aralkyl C$_7$-C$_{20}$, phenyl, phenyl substituted with halogens, —NO$_2$, —CN, —CF$_3$, —CH$_3$, —OCH$_3$; R$^{17}$ = alkyl C$_1$-C$_6$, phenyl, phenyl substituted with halogens, —NO$_2$, —CN, —CF$_3$, —CH$_3$, —OCH$_3$);

R$^1$ = phenyl, phenyl substituted with halogens, —NO$_2$, —CN, —CF$_3$, alkyl, alkoxyl, carbalkoxyl, dialkylaminocarbonyl; aralkyl C$_7$-C$_{20}$; cycloalkyl C$_3$-C$_7$; the —OR$^{18}$ group (where R$^{18}$ = alkyl C$_1$-C$_{10}$; phenyl; phenyl substituted with halogens, alkyl, alkoxy, haloalkyl, —NO$_2$, —CN; aralkyl containing 7-20 carbon atoms, optionally substituted with 1-4 halogens); a

group (where X = O, S and Y = phenyl; phenyl substituted with halogens —NO$_2$, —CN, —CF$_3$, alkyl, alkoxy, aryloxy, arylamino; cycloalkyl C$_3$-C$_6$; heterocycle with 5 or 6 atoms containing 1-4 heteroatoms selected from the group comprising N, O, S; alkyl C$_1$-C$_8$ optionally substituted with 1-11 halogens; an —R$^{19}$—X$^1$—R$^{20}$ group, an —X—R$^{21}$ group; an —R$^{22}$—X$^1$—R$^{23}$—X$^2$—R$^{24}$ group; an —NR$^{25}$R$^{26}$ group, (wherein: R$^{19}$ = alkyl C$_1$-C$_{16}$, aralkyl; R$^{20}$ = alkyl C$_1$-C$_{16}$ optionally substituted with 1-6 halogens, alkenyl C$_3$-C$_6$, alkynyl C$_3$-C$_6$, cycloalkyl C$_3$-C$_7$, phenyl, substituted phenyl, phenylalkyl C$_7$-C$_{13}$; R$^{21}$ = alkyl C$_1$-C$_{16}$ optionally substituted with 1-6 halogens, alkenyl C$_3$-C$_8$, alkynyl C$_3$-C$_6$, cycloalkyl C$_3$-C$_7$, aralkyl, aryl, substituted aryl, —R$^{19}$—X$^1$—R$^{20}$; R$^{22}$, R$^{23}$, R$^{24}$, like or unlike are alkyls C$_1$-C$_{16}$; R$^{25}$, R$^{26}$, like or unlike are H, alkyl C$_1$-C$_{16}$, alkoxyl C$_1$-C$_6$, phenyl optionally substituted with halogens, —NO$_2$, —CN, —CF$_3$, —OCF$_3$, alkyl, alkoxyl, —SO$_2$-alkyl, —SO$_2$-aryl, —CO-aryl-;

X$^1$, X$^2$, like or unlike are O, S, SO, SO$_2$);

n = 0, 1, on condition that when n = 1, R$^1$ = phenyl, substituted phenyl, aralkyl C$_7$-C$_{20}$, cycloalkyl C$_3$-C$_7$.

As for aryl is intended phenyl or naphthyl. Compounds having formula (I) are endowed with biological activity, in particular a herbicidal activity. They are therefore fit to be used in agriculture in the defence of useful crops against weeds.

Compounds having formula (I) can be prepared with known reactions starting for instance, from a compound having formula (II). In particular, compounds having formula (I) where R$^6$ = OH and

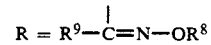

can be prepared according to the following reactions:

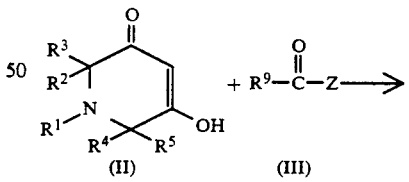

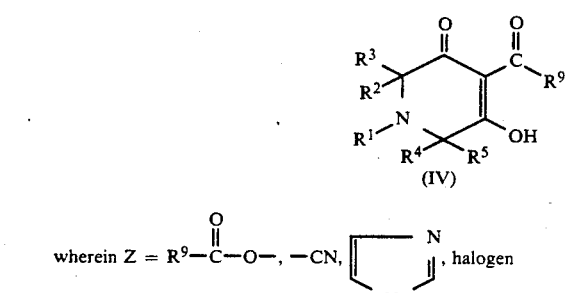

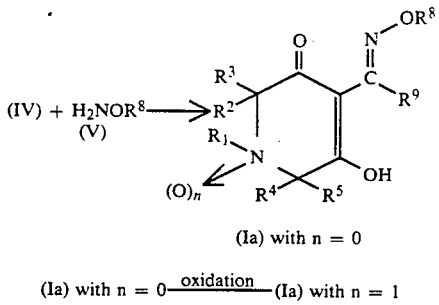

$$(IV) + H_2NOR^8 \longrightarrow \text{(Ia) with } n = 0 \quad (V)$$

(Ia) with n = 0 $\xrightarrow{\text{oxidation}}$ (Ia) with n = 1  3)

According to reaction 1, intermediates (IV) are prepared by reacting compound (II) with an acylating agent having formula (III) in the presence of an organic or inorganic base, or optionally in the presence of bipolar aprotic solvents at temperatures going from 0° C. to the boiling temperature of the reaction mixture.

The acylating agents which can be used are for example anhydrides of carboxylic acids, acyl halides, acylcyanides or an acyl-imidazole.

The base which can be used is for instance sodium hydride, potassium terbutylate, sodium methylate or sodium ethylate.

The solvents which can be used are for example dimethylformamide or dimethyl sulfoxide.

Compounds having formula (II) can in turn be prepared according to well known methods described, for instance, by Y. Tamura, L. C. Chen, M. Fujita and Y. Kita, J. Heterocyclic Chem., 17, 1(1980).

According to reaction 2, intermediates having formula (IV) are caused to react with an oxamino compound (V) in order to produce compounds having formula (Ia) where n=0, in a hydroalcoholic solvent, at temperatures going from 0° C. to the boiling temperature of the reaction mixture, in accordance with a methodology, for example, described in "Organic Functional Group Preparation" Vol. 3, 372-381 (1982) Academic Press-New York.

As for compounds (V), it is possible to use products of deactivation of the corresponding hydrochlorides with a base, such as sodium hydroxide or potassium hydroxide and sodium acetate.

According to reaction 3, compounds having formula (Ia) where n=0 are oxidised to compounds having formula (Ia) where n=1, by using oxidising agents, such as $H_2O_2$ or peracids, in inert organic solvents, such as $CH_2Cl_2$ or $CHCl_3$, at temperatures going from $-20°$ C. to room temperature.

As mentioned above, compounds having formula (I) exhibit interesting biological activities and, in particular, a high herbicidal activity which makes them suitable for using in agriculture in the defence of useful crops against weeds.

Their herbicidal activities appear on a wide range of weeds, furthermore they bear a substantial compatibility or an absence of toxic effects on useful plants in the pre- and post-emergence treatments.

In particular their herbicidal activity has turned out to be decidedly high regarding monocotyledons and the compounds have shown no toxic effect on important agrarian crops like soya, beetroot and cotton. As for their practical use in agriculture, the compounds concerning this invention can be employed as such or, according to normal praxis, under form of an appropriate composition.

In addition to the compound of formula (I), as active principle, inert carriers (which can be both liquid or solid) and if necessary other additives of agrarian use are also present in the compositions.

According to the normal praxis adopted for formulations, compositions may appear under the form of liquid concentrates, emulsifiable concentrates, suspensions, powdered or wettable-powdered compounds and granular compounds.

If one wishes, in order to face specific situations, it is possible to add other active substances which are useful in agriculture such as fertilizers, fungicides or other herbicides to the compositions.

The amount of compound of formula (I) to be used in the defence of useful crops against weeds depends on different factors. Among these, the following can be taken into consideration: the kind and degree of infestation, the type of treatment (whether pre- or post emergence), the relative effectiveness of the specific product of formula (I) also used in relation to the factors mentioned hereinbefore, the kind of crop on which the herbicide treatment is carried out, the formulation used and the climatic and environmental factors.

Generally satisfactory results are obtained by using a quantity of compound of formula (I) going from 0,1 to 3 kg/ha.

The invention will now be illustrated by the following examples.

In the nuclear magnetic resonance spectrum at proton ($^1H$-NMR), as shown in the hereinafter examples, the following abbreviations are used:
S = singlet
dd = doublet of doublets
d = doublet
b = broad
t = triplet
q = quartet
m = multiplet

EXAMPLE 1

Preparation of
1-(2-ethylthiopropanoyl)-4-[1-(ethoximino)butyl]piperidin-3,5-dione. (compound no. 1)

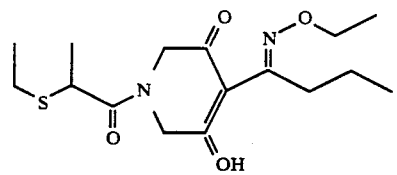

In a 50 ml two-necked flask, supplied with cooler, thermometer and magnetic agitation, 1,5 g of 4-butanoyl-1-(2-ethylthiopropanoyl)piperidin-3,5-dione are introduced. The latter, which is prepared in the hereinafter example 3, is dissolved in 23 ml of water and 1,4 ml of methanol.

At room temperature, 0,49 g of ethoxyamine hydrochloride and 0,41 g of sodium acetate are then added.

The reaction mixture is heated at 50° C. for two hours while the solvent is left to evaporate. The reaction mixture is then diluted in water and extracted with dichloromethane.

The solvent is removed through reduced pressure distillation and the crude product undergoes a silica gel cromatography (dichloromethane eluant) in order to give 0,3 g of product under the form of yellow oil.

¹H-NMR(CDCl₃): 0,95–1.72 (m, 14H, aliphatic); 2.53 (q, 2H, —CH₂S); 3.00 (t, 2H, $$-CH_2\underset{|}{C}=N-);$$

3.62 (q, 1H, $$\underset{}{\overset{}{>}}CHS);$$

4.10 (q, 2H, —CH₂O—); 4.3 (s, 4H, heterocyclic); 14.8 (bs, 1H, —OH).

EXAMPLE 2

Starting from the intermediates described in the hereinafter example 3 and operating under conditions similar to those described in example 1, the following compounds were prepared:

starting from 4-butanoyl-1-(3-methylbutanoyl)piperidin-3, 5-dione and ethoxyamine hydrochloride, the following was prepared: 4-[1-(-ethoximino)butyl]-1-(3-methylbutanoyl) piperidin-3, 5-dione. (compound no. 2)

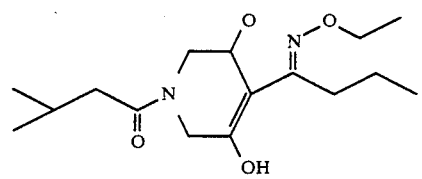

¹H-NMR(CDCl₃): 0.85–1.75 (m, 15H, aliphatic); 2.20 (d, 2H, $$-CH_2\underset{|}{C}=O)$$

2.94 (t, 2H, $$-CH_2\underset{|}{C}=N-);$$

3.73–4.26 (m, 6H, heterocyclic, —CH₂O—); 14.3 (bs, 1H, —OH).

starting-from 4-butanoyl-1-(3-methylbutanoyl)piperidin-3, 5-dione and 3-chloroallyloxyamine hydrochloride, the following was prepared: 4-[1-(3-chloroallyloximino)butyl]-1-(3-methylbutanoyl)piperidin-3,5-dione. (compound no. 3)

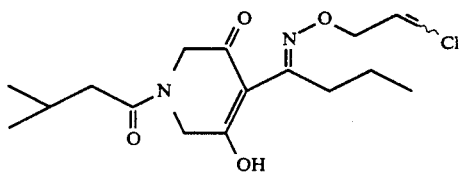

¹H-NMR(CDCl₃): 0.82–1.75 (m, 12H, aliphatic); 2.19 (d, 2H, —CH₂—C═O); 2.93 (t, 2H, —CH₂—C═N—); 4.19–4.28 (m, 4H, heterocyclic); 4.76 (d, 2H, —CH₂O—); 5.81–6.63 (m, 2H, —CH═CHCl); 14.3 (bs, 1H, —OH).

Starting-from 4-butanoyl-1-(n-pentanoyl)piperidin-3,5-dione and ethoxyamine hydrochloride, the following was prepared: 4-[1-(ethoximino)butyl]-1-(n-pentanoyl)piperidin-3, 5-dione. (compound no. 4)

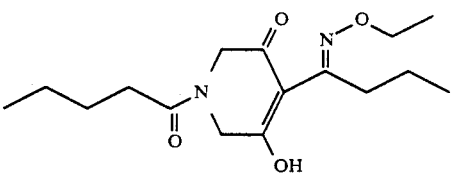

¹H-NMR(CDCl₃): 0.86–1.92 (m, 15H, aliphatic); 2.10–2.61 (m, 2H, $$-CH_2-\underset{|}{C}=O);$$

2.97 (t, 2H, $$-CH_2-\underset{|}{C}=N-);$$

3.84–4.30 (m, 6H, heterocyclic, —CH₂O—); 14,2 (bs, 1H, —OH).

Starting from 4-butanoyl-1-(2-ethylthiopropanoyl) piperidin-3, 5-dione and cis-3-chloroallyloxyamine hydrochloride, the following was prepared: cis-4-[1-(3-chloroallyloximino)butyl]-1-(2-ethylthiopropanoyl)-piperidin-3,5-dione. (compound no. 5)

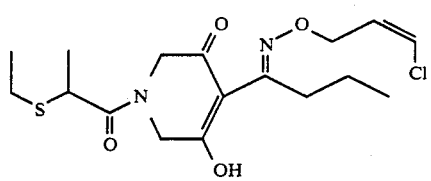

¹H-NMR(CDCl₃): 0.81–1.82 (m, 11H, aliphatic); 2.52 (q, 2H, —CH₂S—); 2.92 (t, 2H, $$-CH_2-\underset{|}{C}=N-);$$

3.61 (q, 1H, $$\underset{}{\overset{}{>}}CH-S-);$$

4.32 (s, 4H, heterocyclic); 4.75(d, 2H, —CH₂O—); 5.80–6.40 (m, 2H, —CH═CHCl); 14.1 (bs, 1H, —OH).

Starting from 4-butanoyl-1-(2-ethylthiopropanoyl) piperidin-3,5-dione and trans-3-chloroallyloxyamine hydrochloride, the following was prepared: trans-4-[1-(3-chloroallyloximino)butyl]-1-(2-ethylthiopropanoyl)-piperidin-3, 5-dione. (compound no. 6).

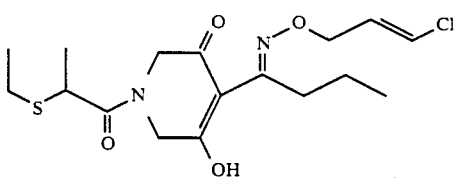

¹H-NMR(CDCl₃): 0.73–1.72 (m, 11H, aliphatic); 2.52 (q, 2H, —CH₂S—); 2.92 (t, 2H,

—CH₂—C=N—);

4.32 (s, 4H, heterocyclic); 4.49 (d, 2H, —CH₂O—); 5.80–6.51 (m, 2H, —CH=CHCl); 14.1 (bs, 1H, —OH).

Starting—from 4-butanoyl-1-(cyclohexanoyl)piperidin-3, 5-dione and ethoxyamine hydrochloride, the following was prepared: 1-(cyclohexanoyl)-4-[1-(ethoximino)butyl] piperidin-3, 5-dione. (compound no. 7).

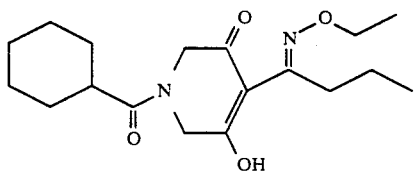

¹H-NMR(CDCl₃): 0.76–1.68 (m, 18H, aliphatic and cycloaliphatic); 2.41 (m, 1H,

>CH—C=O—);

2.96 (t, 2H,

—CH₂—C=N—);

4.10 (q, 2H, —CH₂O—); 4.22 (s, 4H, heterocyclic); 14.4 (bs, 1H, —OH).

Starting—from 4-butanoyl-1-(ethoxycarbonyl)piperidin-3, 5-dione and ethoxyamine hydrochloride, the following was prepared: 1-(ethoxycarbonyl)-4-[1-(ethoximino)butyl] piperidin-3, 5-dione. (compound no. 8)

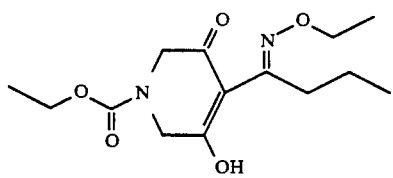

¹H-NMR(CDCl₃): 0.82–1.81 (m, 11H, aliphatic); 2.95 (t, 2H, —CH₂—C=N—); 3.92–4.30 (m, 8H, heterocyclic,

—CH₂—O—C=O, —CH₂—O);

14,3 (bs, 1H, —OH).

Starting from 4-butanoyl-1-(2,4,6-trimethylbenzoyl)piperidin-3, 5-dione and ethoxyamine hydrochloride, the following was prepared: 4-[1-(ethoximino)butyl]-1-(2,4,6-tri methylbenzoyl)piperidin-3, 5-dione. (compound no. 9)

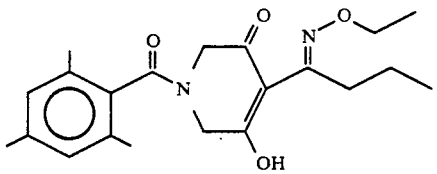

¹H-NMR(CDCl₃): 0.85–1.60 (m, 8H, aliphatic); 2.25 (s, 9H, CH₃ aromatic); 3.03 (t, 2H,

—CH₂—C=N—);

3.90 (s, 2H, heterocyclic); 4.19 (q, 2H, —CH₂O—); 4.62 (s, 2H, heterocyclic); 7.00 (s, 2H, aromatic); 14.42 (bs, 1H, —OH).

Starting from 4-butanoyl-1-(2,4-dichlorobenzoyl)piperidin-3, 5-dione and ethoxyamine hydrochloride, the following was prepared: 1-(2,4-dichlorobenzoyl)-4-[1-(ethoximino)butyl] piperidin-3, 5-dione. (compound no. 10)

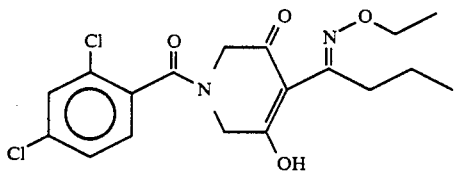

¹H-NMR(CDCl₃): 0.85–1.74 (m, 8H, aliphatic); 3.01 (t, 2H,

—CH₂—C=N—);

3.93 (s, 2H, heterocyclic); 4.12 (q, 2H, —CH₂O—); 4.51 (s, 2H, heterocyclic); 7.30–7.44 (m, 3H, aromatic) 14.62 (bs, 1H, —OH).

Starting—from 4-butanoyl-1-(2,4-dichlorobenzoyl)piperidin-3, 5-dione and cis-3-chloroallyloxyamine hydrochloride, the following was prepared: cis-4-[1-(3-chloroallyloximino)butyl]-1-(2,4-dichlorobenzoyl)-piperidin-3, 5-dione, (compound no. 11)

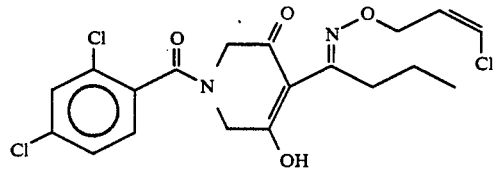

¹H-NMR(CDCl₃): 0.95 (t, 3H, CH₃); 1.48 (m, 2H, —CH₂—CH₃); 2.92 (t, 2H,

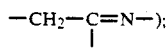

3.88 (s, 2H, heterocyclic);
4.48 (s, 2H, heterocyclic); 4.71 (d, 2H,

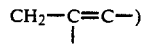

5.78–6.39 (m, 2H, —CH=CHCl); 7.22–7.39 (m, 3H, aromatic); 14.6 (bs, 1H, —OH).

Starting—from 4-butanoyl-1-(2,4-dichlorobenzoyl)-piperidin-3,5-dione and trans-3-chloroallyloxyamine hydrochloride, the following was prepared: trans-4-[1-(3-chloroallyloximino) butyl]1-(2,4-dichlorobenzoyl)-piperidin-3, 5-dione. (compound no. 12)

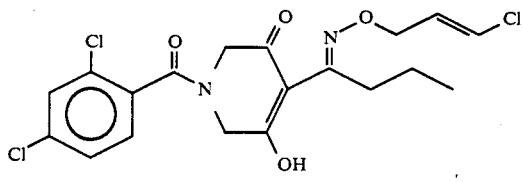

¹H-NMR(CDCl₃): 0.95 (t, 3H, CH₃); 1.54 (m, 2H, —CH₂—CH₃); 2.92 (t, 2H,

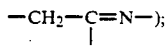

3.91 (s, 2H, heterocyclic); 4.44–4.55 (m, 4H, heterocyclic,

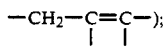

5.85–6.54 (m, 2H, —CH=CHCl); 7.26–7.42 (m, 3H, aromatic) 14.5 (bs, 1H, —OH).

Starting from 4-propanoyl-1-(4-chlorobenzoyl)-piperidin-3, 5-dione and ethoxyamine hydrochloride, the following was prepared: 1-(4-chlorobenzoyl)-4-[1-(ethoximino)propyl] piperidin-3, 5-dione. (compound no. 13)

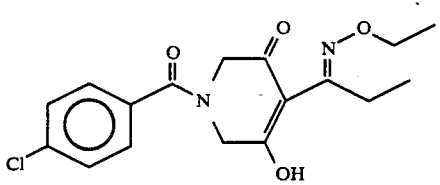

¹H-NMR(CDCl₃): 1.16 (t, 3H, CH₃) 1.35 (t,3H, —CH₃); 3.02 (q, 2H,

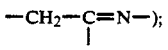

4.10 (q, 2H, q, 2H, CH₂O); 4.30 (s, 4H, heterocyclic); 7.37 (s, 4H, aromatic); 14.61 (bs, 1H, —OH).

Starting—from 4-butanoyl-1-(2,6-dichlorobenzoyl)-piperidin -3, 5-dione and ethoxyamine hydrochloride, the following was prepared: 1-(2,6-dichlorobenzoyl)-4-[1-(ethoximino)butyl] piperidin-3, 5-dione. (compound no. 14)

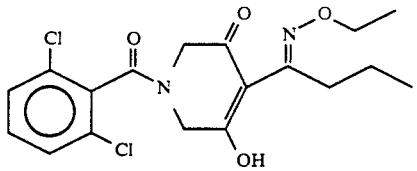

¹H-NMR(CDCl₃): 0.83–1.73 (m, 8H, aliphatic); 2.98 (t, 2H,

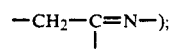

3.85 (s, 2H, heterocyclic); 4.18 (q, 2H, —CH₂O—); 4.51 (s, 2H, heterocyclic); 7.29 (s, 3H, aromatic); 14.10 (bs, 1H, —OH);

Starting from 4-propanoyl-1-(2,6-dichlorobenzoyl) piperidin-3, 5-dione and ethoxyamine hydrochloride, the following was prepared: 1-(2,6-dichlorobenzoyl)-4-[1-(ethoximino)propyl] piperidin-3, 5-dione. (compound no. 15)

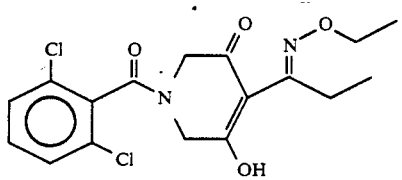

¹H-NMR(CDCl₃): 0.90–1.43 (m, 6H, aliphatic); 2.95 (t, 2H,

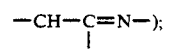

3.89–4.29 (m, 4H, heterocyclic, —CH₂O); 4.52 (s, 2H, heterocyclic); 7.29 (s, 3H, aromatic); 14.12 (bs, 1H, —OH).

Starting from 4-butanoyl-1-(4-nitrobenzoyl)piperidin-3, 5-dione and ethoxyamine hydrochloride, the following was prepared: 4-[1-(ethoximino)butyl]-1-(4-nitrobenzoyl) piperidin-3, 5-dione. (compound no. 16)

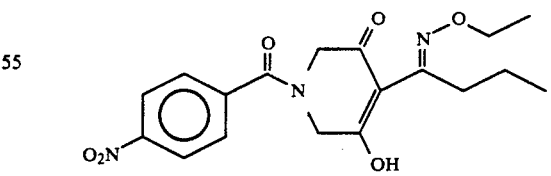

¹H-NMR(CDCl₃): 0.90–1.80 (m, 8H, aliphatic); 3.05 (t, 2H, —CH₂—C=N—); 4.01–4.38 (m, 6H, heterocyclic, —CH₂O); 7.15–8.41 (dd, 4H, aromatic); 14.02 (bs, 1H, —OH).

Starting—from 4-butanoyl-1-(phenyl)piperidin-3, 5-dione and ethoxyamine hydrochloride, the following was prepared: 4-[1-(ethoximino)butyl]-1-(phenyl)piperidin-3, 5-dione. (compound no. 17)

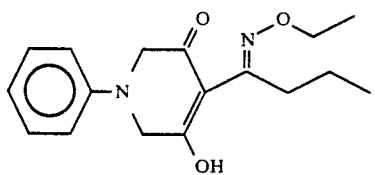

¹H-NMR(CDCl₃): 0.82-1.75 (m, 8H, aliphatic); 2.99 (t, 2H,

—CH₂—C=N—);
|

3.98 (s, 4H, heterocyclic); 4.08 (q, 2H, —CH₂O—); 6.81-7.38 (m, 5H, aromatic); 15.10 (bs, 1H, —OH).

Starting from 4-propanoyl-1-(benzyl)piperidin-3, 5-dione and ethoxyamine hydrochloride, the following was prepared: 1-(benzyl)-4-[1-(ethoximino)propyl]-piperidin-3, 5-dione. (compound no. 18)

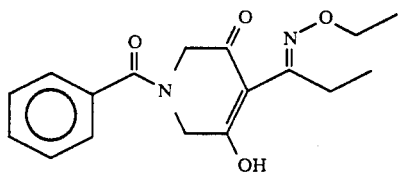

¹H-NMR(CDCl₃): 1.15 (t, 3H, CH₃); 1.28 (t, 3H, —CH₃); 2.98 (q, 2H,

—CH₂—C=N—);
|

3.21 (s, 4H, heterocyclic); 3.56 (s, 2H,

—CH₂—N<);

3.99 (q, 2H, —CH₂O); 7.29 (s, 5H, aromatic); 14.40 (bs, 1H, —OH).

Starting from 4-butanoyl-1-(N,N-dimethylamino carbonyl)piperidin-3,5-dione and ethoxyamine hydrochloride the following compound was prepared: 1-(N,N-dimethylaminocarbonyl)-4-[1-(ethoxyimino)butyl]-piperidin-3,5-dione (compound No. 19).

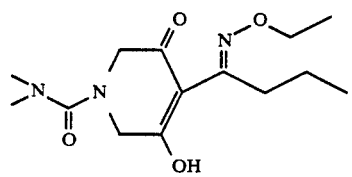

¹H-NMR(CDCl₃): 0.95 (t, 3H, CH₃); 1.2-1.8 (m, 5H, aliphatic); 2.8 (s, 6H, —N(CH₃)₂); 3.0 (t, 2H,

—CH₂—C=N—);
|

3.9 (s, 4H, heterocyclic); 4.1 (q, 2H, —CH₂—O); 14.8 (bs, 1H, OH).

Starting from 4-butanoyl-1-(N,N-dimethylaminocarbonyl)-2-methyl-piperidin-3,5-dione and ethoxyamine hydrochloride the following compound was prepared: 1-(N,N-dimethylaminocarbonyl)-4-[1-(ethoxyimino)-butyl]-2-methyl-piperidin-3,5-dione (compound No. 20)

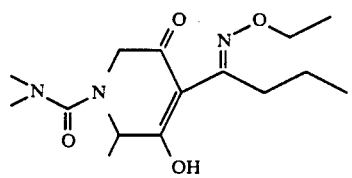

¹H-NMR(CDCl₃): 1.0 (t, 3H, CH₃); 1.3-1.9 (m, 8H, aliphatic); 2.8 (s, 6H, —N(CH₃)₂); 2.9 (t, 2H,

—CH₂—C=N—);
|

3.7-4.5 (m, 5H, heterocyclic and —CH₂—O); 14.4 (s, 1H, OH).

EXAMPLE 3

Preparation of intermediate ketones.

In a 100 ml three-necked flask, which is supplied with a thermometer, cooler and a dropping funnel, 5.85 g of 1-(2-ethylthiopropanoyl)piperidin-3, 5-dione dissolved in 60 ml of anhydrous dimethylformamide are added under nitrogen.

The mixture is heated at 50°-60° C. and 1.22 g of sodium hydride at 50% are added in portions in oil.

When all the gas is evolved, 4.42 g of butyric anhydride are dripped and the remaining mixture is heated at 110° C. for 1½ hours.

The mixture is then diluted with water, extracted with ethyl acetate and dried with sodium sulphate. The solvent is then distilled at reduced pressure.

The crude product then undergoes a silica gel chromatography (eluant: chloroform/methanol 95:5).

1,5 g of 4-butanoyl-1-(2-ethylthiopropanoyl)piperidin-3, 5-dione, having a melting point of 48°-50° C. is obtained:

¹H-NMR(CD₃OD): 0.70-1.27 (m, 11H, aliphatic); 2.22 (t, 2H, —CH₂—S—); 2.55 (t, 2H,

—CH₂—C=O);
|

3.61 (q, 1H,

>CH—S—);

4.48 (s, 4H, heterocyclic); 17.9 (bs, 1H, —OH).

Operating under conditions similar to those described above and starting from 1-(3-methylbutanoyl)piperidin-3, 5-dione and butanoic anhydride, the following compound was obtained: 4-butanoyl-1-(3-methylbutanoyl)-piperidin-3, 5-dione.

¹H-NMR(CD₃OD): 0.89-1.72 (m, 12H, aliphatic); 2.20 (d, 2H,

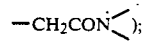

2.75 (t, 2H,

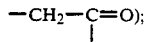

4.20 (s, 4H, heterocyclic); 18.0 (bs, 1H, —OH).

Starting from 1-(n-pentanoyl)piperidin-3, 5-dione and butanoic anhydride, the following was prepared: 4-butanoyl-1-(n-pentanoyl)piperidin-3, 5-dione.

$^1$H-NMR(CDCl$_3$): 0.89–1.78 (m, 12H, aliphatic); 2.29 (m, 4H,

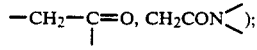

4.12 (s, 4H, heterocyclic); 18.0 (bs, 1H, —OH).

Starting from 1-(cyclohexanoyl)piperidin-3, 5-dione and butanoic anhydride, the following was prepared: 4-butanoyl-1-(ciclohexanoyl)piperidin-3, 5-dione.

$^1$H-NMR(CDCl$_3$): 0.77–1.99 (m, 15H, aliphatic, cycloaliphatic); 2.62 (m, 1H,

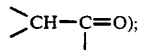

2.90 (t, 2H,

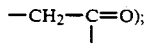

4.25 (s, 4H, heterocyclic); 18.2 (bs, 1H, —OH).

Starting from 1-(ethoxycarbonyl)piperidin-3, 5-dione and butanoic anhydride, the following was prepared: 4-butanoyl-1 (ethoxycarbonyl)piperidin-3, 5-dione.

$^1$H-NMR(CDCl$_3$): 0.80–1.79 (m, 8H, aliphatic); 2.91 (t, 2H,

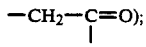

3.90–4.27 (m, 6H, heterocyclic,

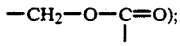

17.8 (bs, 1H, —OH).

Starting from 1-(2, 4, 6-trimethylbenzoyl)piperidin-3, 5-dione and butanoic anhydride, the following was prepared: 4-butanoyl-1-(2,4,6-trimethylbenzoyl)piperidin-3, 5-dione.

$^1$H-NMR(CDCl$_3$): 0.85 (t, 3H, CH$_3$—); 1.47 (m, 2H, —CH$_2$—); 2.09 (s, 6H, aromatic methyls) 2.17 (s, 3H, aromatic methyl) 3.83 (t, 2H,

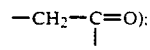

3.81 (s, 2H, heterocyclic); 4.50 (s, 2H, heterocyclic); 6.91 (s, 2H, aromatic); 18.1 (bs, 1H, —OH).

Starting from 1-(2,4-dichlorobenzoyl)piperidin-3, 5-dione and butanoic anhydride, the following was prepared: 4-butanoyl-1-(2,4-dichlorobenzoyl)piperidin-3, 5-dione.

$^1$H-NMR(CD$_3$OD): 0.82 (t, 3H, CH$_3$); 1.46 (m, 2H, —CH$_2$—); 2.99 (t, 2H,

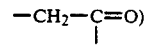

3.79 (s, 2H, heterocyclic); 4.35 (s, 2H, heterocyclic); 7.31–7.44 (m, 3H, aromatic); 18.2 (bs, 1H, —OH).

Starting from 1-(4-chlorobenzoyl)piperidin-3, 5-dione and propanoic anhydride, the following was prepared: 4-propanoyl-1-(4-chlorobenzoyl)piperidin-3, 5-dione.

$^1$H-NMR(CD$_3$OD): 1.15 (t, 3H, CH$_3$); 2.98 (q, 2H,

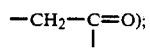

4.28 (s, 4H, heterocyclic); 7.36 (s, 4H, aromatic); 18.0 (bs, 1H, —OH).

Starting from 1-(2,6-dichlorobenzoyl)piperidin-3, 5-dione and butanoic anhydride, the following was prepared: 4-butanoyl-1-(2,6-dichlorobenzoyl)piperidin-3, 5-dione.

$^1$H-NMR(CD$_3$OD): 0.80 (t, 3H, CH$_3$); 1.45 (m, 2H, —CH$_2$—); 3.01 (t, 2H,

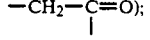

3.74 (s, 2H, heterocyclic); 4.30 (s, 2H, heterocyclic); 7.31 (s, 3H, aromatic); 18.1 (bs, 1H, —OH).

Starting from 1-(2,6-dichlorobenzoyl)piperidin-3, 5-dione and propanoic anhydride, the following was prepared: 4-propanoyl-1-(2,6-dichlorobenzoyl)piperidin-3, 5-dione.

$^1$H-NMR(CD$_3$OD): 0.91 (t, 3H, CH$_3$—); 2.99 (q, 2H,

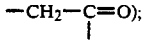

3.75 (s, 2H, heterocyclic); 4.32 (s, 2H, heterocyclic); 7.33 (s, 3H, aromatic); 18.1 (bs, 1H, —OH).

Starting from 1-(4-nitrobenzoyl)piperidin-3, 5-dione and butanoic anhydride, the following was prepared: 4-butanoyl-1-(nitrobenzoyl)piperidin-3, 5-dione.

$^1$H-NMR(DMSO): 0.85 (t, 3H, CH$_3$—); 1.46 (m, 2H, —CH$_2$—); 2.81 (t, 2H,

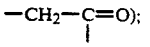

4.25 (s, 4H, heterocyclic); 7.82 (d, 2H, aromatic); 8.44 (d, 2H, aromatic); 18.2 (bs, 1H, —OH);

Starting from 1-(phenyl)piperidin-3, 5-dione and butyric anhydride, the following was prepared: 4-butanoyl-1-(phenyl) piperidin-3, 5-dione.

¹H-NMR(CDCl₃): 0.99 (t, 3H, CH₃—); 1.65 (m, 2H, —CH₂—); 2.91 (t, 2H,

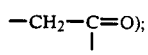

3.91 (s, 2H, heterocyclic); 4.12 (s, 2H, heterocyclic); 6.82-7.30 (m, 5H, aromatic); 17.9 (bs, 1H, —OH).

Starting from 1-(benzyl) piperidin-3,5-dione and propanoic anhydride, the following was prepared: 4-propanoyl-1-(benzyl) piperidin-3,5-dione.

¹H-NMR (DMSO): 0.93 (t, 3H, CH₃—); 2.73 (q, 2H,

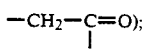

3.00 (s, 4H, heterocyclic); 3.51 (s, 2H,

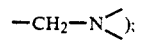

7.29 (s, 5H, aromatic); 18.0 (bs, 1H, —OH).

Starting from 1-(N,N-dimethylaminocarbonyl)piperidin-3,5-dione and butanoic anhydride, the following compound was prepared: 4-butanoyl-1-(N,N-dimethylaminocarbonyl)piperidin-3,5-dione.

¹H-NMR(CDCl₃): 0.75-1.3(m, 5H, aliphatic); 2.4-2.8(m, 2H,

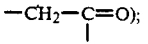

2.8 (s, 6H, —N—(CH₃)₂); 3.9(s, 4H, heterocyclic); 18.0 (bs, 1H, OH).

Starting from 1-(N,N-dimethylamino carbonyl)-2-methyl-piperidin-3,5-dione and butanoic anhydride the following compound was prepared: 4-butanoyl-1-(N,N-dimethylaminocarbonyl)-2-methyl-piperidin-3,5-dione.

¹H-NMR(CDCl₃): 0.8-1.3(m, 5H, aliphatic); 2.3-2.7(m, 2H, —CH₂—C=O); 2.8 (s, 6H, —N—(CH₃)₂); 3.7-4.1(m, 3H, heterocyclic); 18.2 (bs, 1H, OH).

EXAMPLE 4

Determination of the herbicidal activity.

A certain number of pots (dimater over 10 cm and height of 10 cm) containing sandy soil was prepared. In each pot one of the following weeds was sown: Echinochloa Crusgalli, Avena fatua,, Alopecurus Myosuroides, Lolium italicum.

The necessary amount of water was added to each small pot allowing the seeds to germinate well.

The small pots were divided into three groups.

The first group was not treated with any herbicide at all and it was used as a term of comparison (control experiment).

The second group was treated, one day after being sown, with a hydroacetonic dispersion (20% vol./vol.) of the compounds of the invention, in order to evaluate the pre-emergence herbicidal activity.

The third group was treated fifteen days after the seeds had been planted (i.e. when the young plants, in relation to their species, were 10-15 cm tall) with a hydroacetonic dispersion of the compounds of the invention in order to evaluate the post-emergence herbicidal activity.

All the small pots were kept under control in a conditioned environment at temperatures going from 15° C. to 26° C., with a relative humidity=60%, a photoperiod lasting 12 hours and a luminous intensity=5000 lux.

All the pots were equally watered every two days, in order to assure a sufficient percentage of humidity permitting the plants to develop well.

Twenty-eight days after the treatment, the activity of the compounds of the invention was evaluated on the ground of a percentage value scale (0=no herbicidal activity, growth equal to the control experiment; 100=total herbicidal activity, death of plants).

The results obtained using the compounds of the invention, with a dosage of 1 kg/ha of active principle, are reported in Table 1.

TABLE 1

| COMPOUND N° | PRE-EMERGENCE | | | | POST-EMERGENCE | | | |
|---|---|---|---|---|---|---|---|---|
| | ECHINOCHLOA CRUSGALLI | AVENA FATUA | ALOPECURUS MYOSUROIDES | LOLIUM ITALICUM | ECHINOCHLOA CRUSGALLI | AVENA FATUA | ALOPECURUS MYOSUROIDES | LOLIUM ITALICUM |
| 1 | 5 | 5 | 20 | 80 | 100 | 100 | 100 | 100 |
| 2 | 0 | 0 | 25 | 10 | 70 | 100 | 100 | 100 |
| 3 | 5 | 0 | 10 | 30 | 20 | 80 | 95 | 40 |
| 4 | 5 | 0 | 10 | 20 | 15 | 50 | 95 | 90 |
| 5 | 10 | 10 | 35 | 50 | 100 | 100 | 100 | 100 |
| 6 | 10 | 15 | 50 | 60 | 100 | 100 | 100 | 100 |
| 7 | 0 | 0 | 20 | 40 | 70 | 0 | 100 | 75 |
| 8 | 10 | 15 | 90 | 95 | 60 | 60 | 100 | 100 |
| 9 | 5 | 0 | 0 | 60 | 20 | 5 | 20 | 35 |
| 10 | 5 | 0 | 5 | 5 | 20 | 20 | 5 | 10 |
| 11 | 0 | 0 | 0 | 0 | 15 | 10 | 5 | 15 |
| 12 | 0 | 0 | 0 | 0 | 10 | 5 | 0 | 0 |
| 13 | 0 | 0 | 0 | 0 | 100 | 5 | 80 | 25 |
| 14 | 5 | 5 | 5 | 10 | 100 | 60 | 40 | 90 |
| 15 | 0 | 0 | 0 | 0 | 30 | 40 | 35 | 35 |
| 16 | 0 | 0 | 5 | 20 | 45 | 60 | 85 | 75 |
| 17 | 0 | 0 | 0 | 0 | 20 | 25 | 10 | 10 |
| 18 | 0 | 0 | 40 | 90 | 20 | 30 | 30 | 30 |
| 19 | 100 | 100 | 100 | 100 | 100 | 100 | 100 | 100 |

TABLE 1-continued

| COMPOUND N° | PRE-EMERGENCE | | | | POST-EMERGENCE | | | |
| --- | --- | --- | --- | --- | --- | --- | --- | --- |
| | ECHINOCHLOA CRUSGALLI | AVENA FATUA | ALOPECURUS MYOSUROIDES | LOLIUM ITALICUM | ECHINOCHLOA CRUSGALLI | AVENA FATUA | ALOPECURUS MYOSUROIDES | LOLIUM ITALICUM |
| 20 | 100 | 100 | 100 | 100 | 100 | 100 | 100 | 100 |

What we claim is:

1. A process for preparing compounds having the formula (Ia):

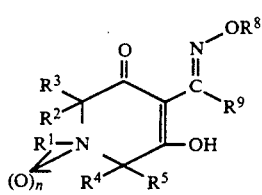

wherein:

$R^1$ is phenyl, phenyl substituted with 1-3 halogen atoms, $-NO_2$, $-CN$, $-CF_3$, $C_1-C_6$ alkoxy;

a

group, wherein X is oxygen or sulfur, and Y is phenyl; phenyl substituted with 1-3 halogen atoms, $-NO_2$, $-CN$, $-CF_3$, $C_1-C_6$ alkyl, $C_1-C_4$ alkoxy, $C_3-C_6$ cycloalkyl; $C_1-C_8$ alkyl, optionally substituted with 1-11 halogen atoms;

an $R^{19}-X^1-R^{20}$ group; an $-X^1-R^{21}$ group; an $R^{22}-X^1-R^{23}-X^2-R^{24}$ group; an $NR^{25}R^{26}$ group wherein $R^{19}$ is $C_1-C_{16}$ alkyl, $C_7-C_{13}$ phenylalkyl, $R^{20}$ is $C_1-C_{16}$ alkyl optionally substituted with 1-6 halogen atoms, $C_3-C_7$ cycloalkyl, phenyl, phenyl substituted with 1-3 halogen atoms, $C_7-C_{13}$ phenylalkyl, $R^{21}$ is $C_1-C_{16}$ alkyl optionally substituted with 1-6 halogen atoms, $C_3-C_8$ alkenyl, $C_3-C_6$ alkynyl, $C_3-C_7$ cycloalkyl, $C_7-C_{13}$ phenylalkyl, phenyl, phenyl substituted with 1-3 halogen atoms, $-NO_2$, $-CN$, $CF_3$ and $-R^{19}-X^1-R^{20}$ group; $R^{22}$, $R^{23}$, and $R^{24}$ are the same or different, from one another, and are $C_1-C_6$ alkyl; $R^{25}$ and $R^{26}$ are the same or different and are H, $C_1-C_6$ alkyl, $C_1-C_6$ alkoxyl, phenyl optionally substituted with 1-3 halogen atoms, $-NO_2$, $-CN$, $-CF_3$, $-OCF_3$, $C_1-C_6$ alkyl, $C_1-C_4$ alkoxy, $-SO_2$-alkyl, $-SO_2$-aryl, $-CO$-aryl;

$X_1$ and $X_2$ are the same or different, from one another, and are selected from the group consisting of O, S, SO, and $SO_2$;

n is 0 or 1 on the condition that when n is 1, $R^1$ is selected from the group consisting of phenyl, phenyl substituted with 1-3 halogen atoms, $C_1-C_6$ alkyl, $C_1-C_6$ alkoxy $-NO_2$, $-CN$, $-CF_3$, $C_7-C_{20}$ aralkyl and $C_3-C_7$ cycloalkyl;

$R^2$, $R^3$, $R^4$ and $R^5$ are the same or different, from one another, and represent H, $C_1-C_3$ alkyl;

$R^8$ is $C_1-C_6$ alkyl, $C_1-C_6$ alkyl substituted with 1-4 halogen atoms, $C_2-C_6$ alkenyl, $C_2-C_6$ alkenyl substituted with 1-4 halogen atoms, $C_3-C_6$ alkynyl, $C_3-C_7$ cycloalkyl;

$R^9$ is $C_1-C_6$ alkyl, $C_3-C_6$ cycloalkyl, phenyl, phenyl substituted with 1-3 halogen atoms, $-CN$, $-NO_2$, $-CH_3$, $-SOCH_3$, $-OCH_3$, or $-CF_3$; consisting of:

a) reacting a compound of the formula

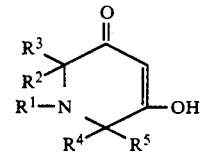

with an acylating agent of the formula;

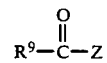

in the presence of a base, at temperature from 0° C. to the boiling point of the reaction mixture and, optionally, in a dipolar solvent to obtain compounds of the formula:

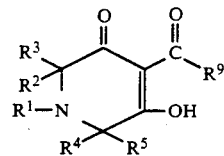

wherein $R^1$, $R^2$, $R^3$, $R^4$, $R^5$ and $R^9$ have meaning as specified above and Z is

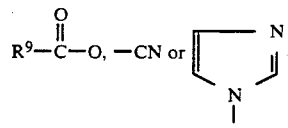

or halogen, b) reacting the compound produced in step a) with an oxaminic compound of the formula $H_2NOR^8$ in a hydroalcoholic solvent, at temperatures from 0° C. to the boiling point of the reaction mixture to obtain a compound of the formula:

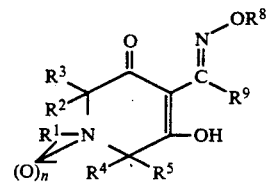

wherein $R^2$, $R^3$, $R^4$, $R^5$, $R^8$ and $R^9$ have meaning as specified above and n is zero, and optionally c) oxidizing compounds produced in step b) with a peroxidic oxidant, in an inert solvent, at a temperature from $-20°$ C. to room temperature to produce compounds wherein n=1.

* * * * *